United States Patent [19]
Cevasco et al.

[11] Patent Number: 5,942,640
[45] Date of Patent: Aug. 24, 1999

[54] PROCESS FOR THE MANUFACTURE OF N-(1-CYANOALKYL)-2-PHENOXYPROPIONAMIDE DERIVATIVES

[75] Inventors: Albert Anthony Cevasco, Belle Mead; Kenneth Alfred Martin Kremer, Lawrenceville, both of N.J.

[73] Assignee: American Cyanamid Company, Madison, N.J.

[21] Appl. No.: 09/062,975

[22] Filed: Apr. 20, 1998

[51] Int. Cl.$^6$ .................................................. C07C 255/00
[52] U.S. Cl. ............................................................ 558/393
[58] Field of Search ............................................ 558/393

[56] References Cited

U.S. PATENT DOCUMENTS

| | | |
|---|---|---|
| 3,932,168 | 1/1976 | Stein et al. . |
| 4,052,432 | 10/1977 | Baker et al. . |
| 4,087,277 | 5/1978 | Baker et al. . |

FOREIGN PATENT DOCUMENTS

| | | |
|---|---|---|
| 1311240 | 8/1987 | Canada . |
| 5-9165 | 1/1993 | Japan . |
| 5-70428 | 3/1993 | Japan . |

OTHER PUBLICATIONS

Research Disclosure 92–306005

*Primary Examiner*—Johann Richter
*Assistant Examiner*—Joseph Murray
*Attorney, Agent, or Firm*—C. F. Costello, Jr.

[57] ABSTRACT

The present invention provides an efficient, economic and ecologically sound process for the manufacture of a compound of formula I via the reaction of a suitable acid halide and an appropriate amine in the presence of aqueous carbonate or bicarbonate or a mixture thereof and optionally in the presence of a co-solvent.

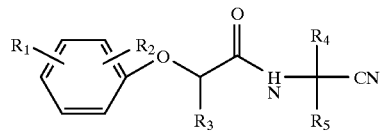

(I)

10 Claims, No Drawings

PROCESS FOR THE MANUFACTURE OF N-(1-CYANOALKYL)-2-PHENOXYPROPIONAMIDE DERIVATIVES

BACKGROUND OF THE INVENTION

Arylcarboxylic acid derivatives, in particular N-(1-cyanoalkyl)-2-phenoxypropionamide derivatives are useful for combatting phytopathogenic fungi and are described in CA 1,311,240.

In general, known processes to prepare the fungicidal N-(1-cyanoalkyl)-2-phenoxypropionamide derivatives such as that described in Research Disclosure 92306005 entail a non-aqueous system utilizing an organic amine base, such as a trialkylamine. However, on a manufacturing scale, use of irritants such as volatile organic amines leads to large quantities of effluent which require costly treatment and recovery steps. An alternate known process to prepare said propionamide derivatives is that described in Japanese patent application publication Kokai No. 5-9165 which utilizes 10% aqueous NaOH as the base. However, use of a strong base such as NaOH increases the rate of formation of undesired side-products such as the formation of the corresponding phenoxypropionic acid of the starting acid chloride. This unwanted by-product is not carried on to the desired amide product. Further, said acid by-product is a known herbicide derivative, and would, therefore, contaminate the desired fungicidal product with a phytotoxic compound. This contamination would be detrimental to the use of the product in crop production practice.

Therefore, it is an object of the present invention to provide an improved, economic and efficient process for the manufacture of N-(1-cyanoalkyl)-2-phenoxypropionamide derivatives. It is a feature of this invention that said propionamide derivatives are produced in higher yield and improved purity.

Other objects and features of the invention will become apparent from the detailed description set forth hereinbelow.

SUMMARY OF THE INVENTION

The present invention provides an improved process for the manufacture of a compound of formula I

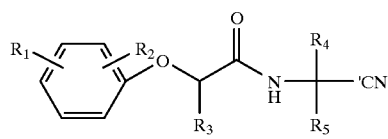

wherein $R_1$ and $R_2$ are each independently H, halogen, $C_1$–$C_6$alkyl or $C_6$–$C_6$haloalkyl;

$R_3$ is H or $C_1$–$C_4$alkyl; and $R_4$ and $R_5$ are each independently H, $C_1$–$C_6$alkyl, $C_1$–$C_6$haloalkyl or $C_3$–$C_6$cyclooalkyl; and the optical isomers thereof which comprises reacting a phenoxy acid halide compound of formula II

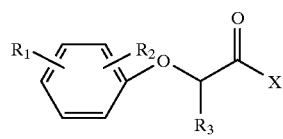

wherein X is halogen and $R_1$, $R_2$ and $R_3$ are as described for formula I with at least one molar equivalent of an amino nitrile compound of formula III

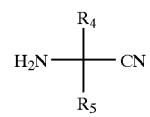

wherein $R_4$ and $R_5$ are as described for formula I in the presence of aqueous alkali metal carbonate or aqueous alkali metal bicarbonate or a mixture thereof, optionally in the presence of a co-solvent.

Compounds of formula I are useful as phytopathogenic fungicidal agents.

DETAILED DESCRIPTION OF THE INVENTION

Compounds of formula I have been prepared via an organic base such as a trialkylamine or a strong base such as NaOH. However, on a manufacturing scale, organic amines which may be irritating and hazardous, require costly treatment and recovery steps. Further, strong bases such as NaOH, increase the rate of formation of undesired side-products such as the corresponding acid of the formula II starting acid halide and degradation of the starting amino nitrile compounds of formula III, resulting in decreased product yield and purity. It has now been found, that use of aqueous alkali metal carbonates or bicarbonates or mixtures thereof, yield excellent results on a manufacturing scale for the production of the formula I propionamide fungicidal agents. Preferable alkali metal carbonates or bicarbonates suitable for use in the process of the invention are $Na_2CO_3$, $K_2CO_3$, $NaHCO_3$ or $KHCO_3$ or mixtures thereof.

Hence, N-(1-cyanoalkyl)-2-phenoxypropionamide, derivatives of formula I may be prepared in good yield and purity by reacting a phenoxypropionyl halide of formula II with at least one molar equivalent of an amino nitrile of formula III in the presence of an aqueous alkali metal carbonate or aqueous alkali metal bicarbonate or a mixture thereof, preferably $NaHCO_3$ or $KHCO_3$, optionally in the presence of a solvent. The reaction is shown in flow diagram I wherein M represents an alkali metal.

Flow Diagram I

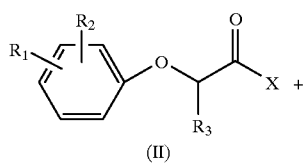

-continued

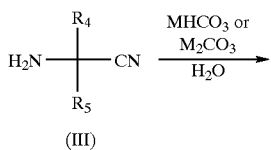

(III)

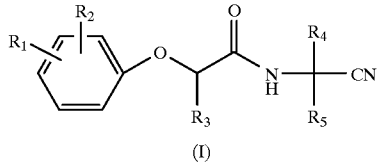

(I)

The rate of formation of the formula I product is directly related to the reaction temperature. Lower reaction temperatures result in increased reaction time. Higher reaction temperatures decrease reaction time and increase reaction rate. However, increased temperatures may also lead to undesirable side reactions and the resultant formation of undesirable by-products. Advantageously, it has been found that the process of the invention is robust, that is, it is efficient over a wide range of temperatures, preferably about 0°–30° C., more preferably about 0°–15° C.

Co-solvents suitable for use in the process of the invention may be any inert, water immiscible solvent for example aromatic hydrocarbons such as toluene, benzene, xylene, or the like, preferably toluene; halogenated aromatic hydrocarbons such as chlorobenzene; halogenated hydrocarbons such as methylene chloride, dichloroethane and the like; ethers such as ethyl acetate, methyl propionate and the like.

Compounds of formula II may be readily obtained from their corresponding acid precursors or purchased commercially. Preferable formula II compounds are those compounds wherein X is Cl or Br. Compounds of formula III may be obtained via conventional methods or purchased commercially.

The mode of addition of the reactants of formula II and formula III in accordance with the process of the invention may be either sequential or simultaneous, preferably simultaneous.

Advantageously, the process of the invention yields retention of configuration around an assymetric carbon, when optically active starting materials are employed. For example, (R)-2-phenoxypriopionyl halide derivatives of formula II, when reacted with a racemic amino nitrile of formula III in accordance with the process of the invention yields a formula I propionamide product having predominantly the RS and RR configurations. Similarly, the (R)-phenoxypropionyl halide when reacted with (R)-(amino nitrile) in accordance with the process of the invention, yields a formula I propionamide product having predominantly the RR configuration.

In order to facilitate a further understanding of the invention, the following examples are set forth primarily for the purpose of illustrating certain more specific details thereof. The invention is not to be limited thereby except as defined in the claims. The term HPLC designates high pressure liquid chromatography.

EXAMPLE 1

Preparation of (R)-2-(2,4-Dichlorophenoxy) propionyl chloride

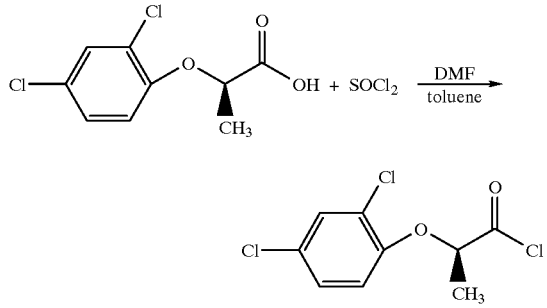

A stirred mixture of (R)-2-(2,4-dichlorophenoxy) propionic acid (588 g, 2.5 mol), 588 g of toluene and 0.6 g of dimethyl formamide (DMF) is heated to 75° C., treated with thionyl chloride (304 g, 2.55 mol) over a 1.5 hour period, heated at 75° C. for 1 hour and cooled to 20–25° C. The resultant reaction mixture may be distilled to obtain the title product in quantitative yield, as an amber oil, or used as is in the next process step. The isolated product is characterized by NMR analysis. The product toluene solution is assayed by HPLC analysis.

EXAMPLE 2

Preparation of N-(1-Cyano-1,2-dimethylpropyl)-2-(2,4-dichlorophenxoy) propionamide via simultaneous addition

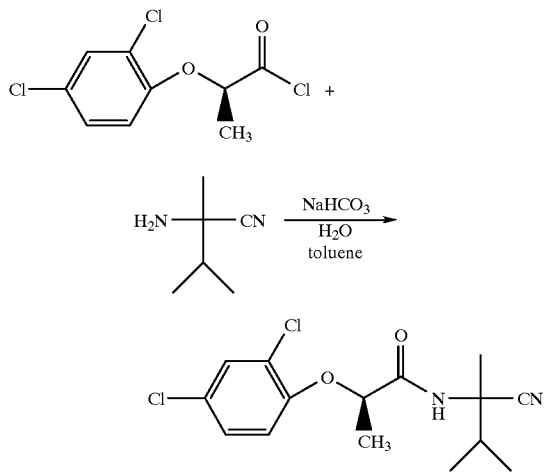

A stirred mixture of sodium bicarbonate (8.40 g, 0.10 mole), water and toluene is treated simultaneously with a solution of 2-amino-2,3-dimethylbutyronitrile (5.89 g, 0.0525 mol) in toluene and (R)-2-(2,4dichlorophenoxy) propionyl chloride (12.7 g, 0.05 mol) at a temperature range of 23° to 28° C., stirred for 0.5 hours at ambient temperatures and allowed to stand. The phases are separated. The organic phase is wished sequentially with water, 5% NaOH and brine and distilled in vacuo to 74° C./0.1 mm Hg to remove the solvent and afford the title product as an amber oil, 16.29 g (97.6% pure, 96.7% yield) identified by HPLC analysis. Isomer content is: 47.1% RR, 46.6% RS, 2.4% SS and 2.9% SR.

EXAMPLE 3

Preparation of N-(1-Cyano-1,2-dimethylpropyl)-2-(2,4-dichlorophenoxy)propionamide via sequential addition

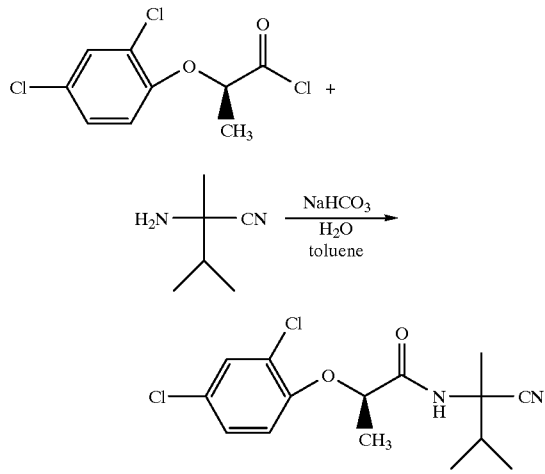

A stirred mixture of sodium bicarbonate (1.446 kg; 17.2 mol) in water at -3° to 3° C. is treated with a toluene solution of 2-amino-2,3-dimethylbutyronitrile (1.51 kg, 13.46 mol) over a 15 minute period, then treated sequentially with a toluene solution of (R)-2-(2,4-dichlorophenoxy) propionyl chloride (3.346 kg, 13.2 mol) over a 1.5 hour period at ice bath temperatures, stirred for 0.5 hours, treated with 50% NaOH (0.396 kg), heated to 55° C. and stirred for 0.5 hours. The resultant mixture is separated. The organic phase is washed with 5% NaOH and distilled at temperatures up to 80° C. at 10 mm Hg to remove the toluene. The pot residue is crystallized in isopropanol/water to afford the title product as a white solid, 4.131 kg (94.8% yield), characterized by HPLC analysis. The product is 99.7% pure. The isomer ratio is: 94.8% RR, RS and 5.2% SS, SR.

EXAMPLE 4

Preparation of (R,R)-N-1-Cyano-1,2-dimethylpropyl)-2-(2,4-dichlorophenoxy)propionamide

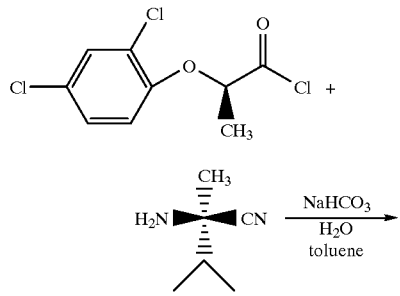

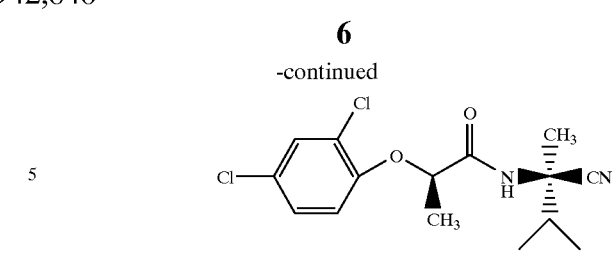

A stirred mixture of sodium bicarbonate (27.3 g, 0.325 mol) in water at 3°–8° C. is treated simultaneously with a toluene solution of (R)-2-amino-2,3-dimethylbutyrontrile (31.08 g, 0.27 mol) and a toluene solution of (R)-3-(2,4-dichlorophenoxy)propionyl chloride (61.16 g, 0.237 mol) over a 1.5 hour period at ice bath temperatures, stirred for 1 hour, treated with 50% NaOH (7.6 g), heated to 55° C. and stirred for 0.5 hours. The reaction mixture is separated and the organic phase is washed with 10% NaOH and distilled (102° C./65 mm Hg) to remove the toluene. The residue is crystallized in isopropanol/water to afford the title product as a white solid 75.5 g (96% yield of all isomers), identified by HPLC analysis to contain 88.9% RR, 6.5% RS, 0% SS and 4.5% SR. The product is 98.7% pure.

EXAMPLE 5

Preparation of (R,S)-N-(1-Cyano-1,2-dimethylpropyl)-2-(2,4-dichlorophenoxy)propionamide

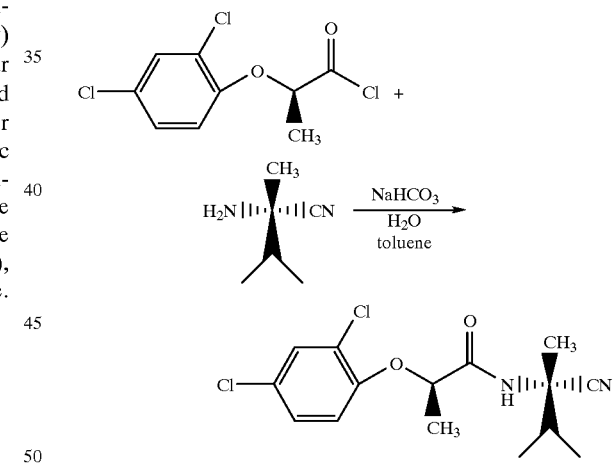

A stirred mixture of sodium bicarbonate (26.4 g, 0.31 mol) in water at 3°–8° C. is treated simultaneously with a toluene solution of (S)-2-amino-2,3-dimethylbutyronitrile (28.47 g, 0.25 mol) and a toluene solution of (R)-3-(2,4-dichlorophenoxy) propionyl chloride (58.23 g, 0.23 mol) over a 0.5 hour period, stirred for 1 hour at 5°–10° C., treated with 50% NaOH (7.6 g), heated to 55° C. and stirred for 0.5 hour. The resultant reaction mixture is separated and the organic phase is distilled (104° C./65 mm Hg) to remove the toluene. The pot residue is crystallized in isopropanol/water to afford the title product as a white solid, 71.5 g (93% yield of all isomers). HPLC analysis shows the product is 96.8% pure with an isomer ratio of 90.6% RS, 5.5% RR, 3.9% SS and 0% SR.

EXAMPLE 6

- Comparative Example A

Preparation of N-(1-Cyano-1,2-dimethylpropyl)-2-(2,4-dichlorophenoxy)propionamide via a non-aqueous system

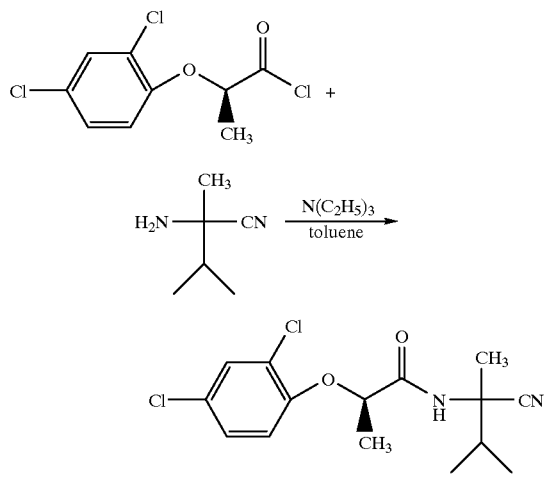

A stirred solution of (R)-2-(2,4-dichlorophenoxy) propionyl chloride (380.25 g, 1.5 mol) in toluene is cooled to -10° C. and treated simultaneously, with cooling, with 2-amino-2,3-dimethylbutyronitrile (168.3 g, 1.5 mol) and triethylamine (181.8 g, 1.8 mol) so as to maintain a reaction temperature range of -5° C. to -10° C. When the simultaneous addition of amines is complete, the reaction mixture is stirred at -5° C. for 2 hours, allowed to warm to room temperature in the absence of external heating, and treated with water. The phases are separated. The organic phase is cooled to 0° C., treated with 10% NaOH, and stirred for 1 hour at 0° C. The phases are separated. The organic phase is again washed with fresh 10% NaOH for 1 hour at 0° C., separated and washed a third time at 0° C. for 1 hour with fresh 10% NaOH. The organic phase is then washed sequentially with water, brine and water, dried over MgSO$_4$ and concentrated in vacuo to give a residue. The residue is crystallized in petroleum ether to give the title product as a white solid, 435 g (88% yield) identified by NMR analysis.

EXAMPLE 7

- Comparative Example B

Preparation of N-(1-Cyano-1,2-dimethylpropyl)-2-(2,4-dichlorophenoxy)propionamide via use of aqueous NaOH

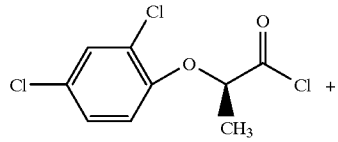

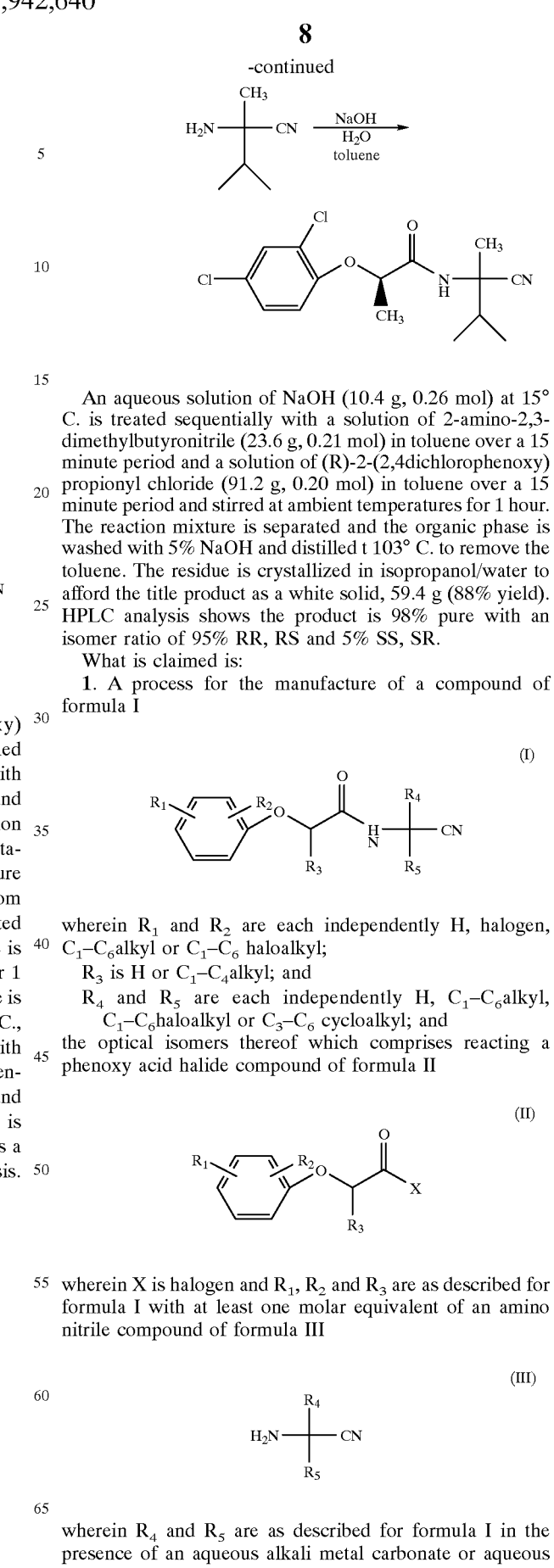

An aqueous solution of NaOH (10.4 g, 0.26 mol) at 15° C. is treated sequentially with a solution of 2-amino-2,3-dimethylbutyronitrile (23.6 g, 0.21 mol) in toluene over a 15 minute period and a solution of (R)-2-(2,4dichlorophenoxy) propionyl chloride (91.2 g, 0.20 mol) in toluene over a 15 minute period and stirred at ambient temperatures for 1 hour. The reaction mixture is separated and the organic phase is washed with 5% NaOH and distilled t 103° C. to remove the toluene. The residue is crystallized in isopropanol/water to afford the title product as a white solid, 59.4 g (88% yield). HPLC analysis shows the product is 98% pure with an isomer ratio of 95% RR, RS and 5% SS, SR.

What is claimed is:

1. A process for the manufacture of a compound of formula I wherein $R_1$ and $R_2$ are each independently H, halogen, $C_1$-$C_6$alkyl or $C_1$-$C_6$ haloalkyl;

$R_3$ is H or $C_1$-$C_4$alkyl; and $R_4$ and $R_5$ are each independently H, $C_1$-$C_6$alkyl, $C_1$-$C_6$haloalkyl or $C_3$-$C_6$ cycloalkyl; and the optical isomers thereof which comprises reacting a phenoxy acid halide compound of formula II wherein X is halogen and $R_1$, $R_2$ and $R_3$ are as described for formula I with at least one molar equivalent of an amino nitrile compound of formula III wherein $R_4$ and $R_5$ are as described for formula I in the presence of an aqueous alkali metal carbonate or aqueous alkali metal bicarbonate, or a mixture thereof, and optionally in the presence of a co-solvent.

2. The process according to claim 1 in the presence of a co-solvent.

3. The process according to claim 2 wherein the co-solvent is water immiscible.

4. The process according to claim 1 wherein X is Cl or Br.

5. The process according to claim 1 wherein the alkali metal is sodium or potassium or a mixture thereof.

6. The process according to claim 1 or 2 or 3 for the manufacture of a formula I compound in the R configuration, wherein the formula II compound is in the R configuration at the $R_3$ position.

7. The process according to claim 1 for the manufacture of a formula I compound wherein $R_1$ and $R_2$ are each independently halogen.

8. The process according to claim 7 for the manufacture of a compound of formula 1 wherein $R_3$ and $R_4$ are methyl and $R_5$ is isopropyl.

9. The process according to claim 8 wherein X is Cl.

10. The process according to claim 2 or 3 or 8 wherein the formula II and formula III compounds are reacted in the presence of aqueous sodium bicarbonate and toluene.

* * * * *

UNITED STATES PATENT AND TRADEMARK OFFICE
CERTIFICATE OF CORRECTION

PATENT NO. : 5,942,640
DATED : August 24, 1999
INVENTOR(S) : Cevasco et al.

It is certified that error appears in the above-identified patent and that said Letters Patent is hereby corrected as shown below:

Column 3,
Line 34, delete "ethers" and substitute -- esters --.

Signed and Sealed this

Eleventh Day of December, 2001

Attest:

NICHOLAS P. GODICI
Attesting Officer
Acting Director of the United States Patent and Trademark Office